(12) United States Patent
Cowley

(10) Patent No.: US 11,246,621 B2
(45) Date of Patent: *Feb. 15, 2022

(54) ULTRASONIC TRANSDUCERS AND ULTRASONIC SURGICAL INSTRUMENTS INCLUDING THE SAME

(71) Applicant: COVIDIEN LP, Mansfield, MA (US)

(72) Inventor: Matthew S. Cowley, Frederick, CO (US)

(73) Assignee: Covidien LP, Mansfield, MA (US)

( * ) Notice: Subject to any disclaimer, the term of this patent is extended or adjusted under 35 U.S.C. 154(b) by 97 days.

This patent is subject to a terminal disclaimer.

(21) Appl. No.: 16/048,953

(22) Filed: Jul. 30, 2018

(65) Prior Publication Data

US 2019/0231385 A1 Aug. 1, 2019

Related U.S. Application Data

(63) Continuation-in-part of application No. 15/882,375, filed on Jan. 29, 2018.

(51) Int. Cl.
*A61B 17/32* (2006.01)
*A61B 17/00* (2006.01)

(52) U.S. Cl.
CPC ............ *A61B 17/320092* (2013.01); *A61B 17/320068* (2013.01); *A61B 2017/0011* (2013.01); *A61B 2017/00026* (2013.01); *A61B 2017/320074* (2017.08); *A61B 2017/320094* (2017.08); *A61B 2017/320095* (2017.08)

(58) Field of Classification Search
CPC .... A61B 17/320068; A61B 17/320092; A61B 2017/320074; A61B 2017/320094; A61B 2017/00026; A61B 2017/0011; A61B 2017/00402; A61B 2017/00929; A61B 2017/22027; A61B 2017/320095
See application file for complete search history.

(56) References Cited

U.S. PATENT DOCUMENTS

| | | | |
|---|---|---|---|
| 1,813,902 | A | 7/1931 | Bovie |
| 2,235,274 | A | 3/1941 | Trehern |
| 2,874,470 | A | 2/1959 | Richards |
| 2,990,616 | A | 7/1961 | Balamuth |
| 3,432,691 | A | 3/1969 | Shoh |
| 3,489,930 | A | 1/1970 | Shoh |
| 3,526,792 | A | 9/1970 | Shoh |

(Continued)

FOREIGN PATENT DOCUMENTS

| | | |
|---|---|---|
| EP | 0705570 A1 | 4/1996 |
| EP | 0908148 A1 | 4/1999 |

(Continued)

*Primary Examiner* — Tigist S Demie
(74) *Attorney, Agent, or Firm* — Carter, DeLuca & Farrell LLP

(57) ABSTRACT

An ultrasonic transducer for an ultrasonic surgical instrument includes a proximal hub, a piezoelectric rod array including a plurality of piezoelectric rods spaced-apart from one another and disposed in parallel and longitudinally-extending orientation relative to one another, and a distal horn including a distal connector configured to engage a waveguide. The proximal hub and the distal horn are configured to engage one another to retain the piezoelectric rod array therebetween under compression.

19 Claims, 5 Drawing Sheets

(56) References Cited

U.S. PATENT DOCUMENTS

| | | |
|---|---|---|
| 3,629,726 A | 12/1971 | Popescu |
| 3,668,486 A | 6/1972 | Silver |
| 3,809,977 A | 5/1974 | Balamuth et al. |
| 3,875,945 A | 4/1975 | Friedman |
| 3,924,335 A | 12/1975 | Balamuth et al. |
| 4,012,647 A | 3/1977 | Balamuth et al. |
| 4,193,818 A | 3/1980 | Young et al. |
| 4,227,110 A | 10/1980 | Douglas et al. |
| 4,300,083 A | 11/1981 | Heiges |
| 4,302,728 A | 11/1981 | Nakamura |
| 4,370,302 A | 1/1983 | Suzuoka et al. |
| 4,641,053 A | 2/1987 | Takeda |
| 4,683,396 A | 7/1987 | Takeuchi et al. |
| 5,113,116 A | 5/1992 | Wilson |
| 5,224,680 A | 7/1993 | Greenstein et al. |
| 5,264,925 A | 11/1993 | Shipp et al. |
| 5,275,166 A | 1/1994 | Vaitekunas et al. |
| 5,374,813 A | 12/1994 | Shipp |
| 5,394,187 A | 2/1995 | Shipp |
| 5,408,268 A | 4/1995 | Shipp |
| 5,451,220 A | 9/1995 | Ciervo |
| 5,490,860 A | 2/1996 | Middle et al. |
| 5,565,520 A | 10/1996 | Fock et al. |
| 5,582,617 A | 12/1996 | Klieman et al. |
| 5,593,414 A | 1/1997 | Shipp et al. |
| 5,685,311 A | 11/1997 | Hara |
| 5,717,306 A | 2/1998 | Shipp |
| 5,728,130 A | 3/1998 | Ishikawa et al. |
| 5,776,155 A | 7/1998 | Beaupre et al. |
| 5,792,138 A | 8/1998 | Shipp |
| 5,796,056 A | 8/1998 | Bredow et al. |
| 5,810,859 A | 9/1998 | DiMatteo et al. |
| 5,858,018 A | 1/1999 | Shipp et al. |
| 5,873,873 A | 2/1999 | Smith et al. |
| 5,897,569 A | 4/1999 | Kellogg et al. |
| 5,910,152 A | 6/1999 | Bays |
| 5,938,633 A | 8/1999 | Beaupre |
| 5,944,737 A | 8/1999 | Tsonton et al. |
| 5,947,984 A | 9/1999 | Whipple |
| 5,954,736 A | 9/1999 | Bishop et al. |
| 5,993,465 A | 11/1999 | Shipp et al. |
| 5,994,855 A | 11/1999 | Lundell et al. |
| 6,031,526 A | 2/2000 | Shipp |
| 6,036,667 A | 3/2000 | Manna et al. |
| 6,068,647 A | 5/2000 | Witt et al. |
| 6,095,981 A | 8/2000 | McGahan |
| 6,162,194 A | 12/2000 | Shipp |
| 6,183,426 B1 | 2/2001 | Akisada et al. |
| 6,220,098 B1 | 4/2001 | Johnson et al. |
| 6,225,728 B1 | 5/2001 | Gururaja |
| 6,254,623 B1 | 7/2001 | Haibel, Jr. et al. |
| 6,257,241 B1 | 7/2001 | Wampler |
| 6,278,218 B1 | 8/2001 | Madan et al. |
| 6,280,407 B1 | 8/2001 | Manna et al. |
| 6,283,981 B1 | 9/2001 | Beaupre |
| 6,284,185 B1 | 9/2001 | Tokuda et al. |
| 6,287,344 B1 | 9/2001 | Wampler et al. |
| 6,290,575 B1 | 9/2001 | Shipp |
| 6,306,157 B1 | 10/2001 | Shchervinsky |
| 6,309,400 B2 | 10/2001 | Beaupre |
| 6,325,811 B1 | 12/2001 | Messerly |
| 6,328,751 B1 | 12/2001 | Beaupre |
| 6,350,269 B1 | 2/2002 | Shipp et al. |
| 6,352,532 B1 | 3/2002 | Kramer et al. |
| 6,416,486 B1 | 7/2002 | Wampler |
| 6,423,082 B1 | 7/2002 | Houser et al. |
| 6,432,118 B1 | 8/2002 | Messerly |
| 6,443,968 B1 | 9/2002 | Holthaus et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,482,220 B1 | 11/2002 | Mueller |
| 6,483,228 B2 | 11/2002 | Hashimoto |
| 6,491,708 B2 | 12/2002 | Madan et al. |
| 6,500,188 B2 | 12/2002 | Harper et al. |
| 6,514,267 B2 | 2/2003 | Jewett |
| 6,537,291 B2 | 3/2003 | Friedman et al. |
| 6,561,983 B2 | 5/2003 | Cronin et al. |
| 6,565,520 B1 | 5/2003 | Young |
| 6,588,277 B2 | 7/2003 | Giordano et al. |
| 6,589,200 B1 | 7/2003 | Schwemberger et al. |
| 6,607,540 B1 | 8/2003 | Shipp |
| 6,623,500 B1 | 9/2003 | Cook et al. |
| 6,626,926 B2 | 9/2003 | Friedman et al. |
| 6,633,234 B2 | 10/2003 | Wiener et al. |
| 6,652,539 B2 | 11/2003 | Shipp et al. |
| 6,652,545 B2 | 11/2003 | Shipp et al. |
| 6,660,017 B2 | 12/2003 | Beaupre |
| 6,662,127 B2 | 12/2003 | Wiener et al. |
| 6,666,875 B1 | 12/2003 | Sakurai et al. |
| 6,671,230 B1 | 12/2003 | Benjamin |
| 6,678,621 B2 | 1/2004 | Wiener et al. |
| 6,679,899 B2 | 1/2004 | Wiener et al. |
| 6,719,776 B2 | 4/2004 | Baxter et al. |
| 6,752,815 B2 | 6/2004 | Beaupre |
| 6,773,444 B2 | 8/2004 | Messerly |
| 6,869,439 B2 | 3/2005 | White et al. |
| 6,908,472 B2 | 6/2005 | Wiener et al. |
| 6,915,623 B2 | 7/2005 | Dey et al. |
| 6,945,981 B2 | 9/2005 | Donofrio et al. |
| 6,976,969 B2 | 12/2005 | Messerly |
| 7,037,306 B2 | 5/2006 | Podany et al. |
| 7,066,895 B2 | 6/2006 | Podany |
| 7,074,218 B2 | 7/2006 | Washington et al. |
| 7,108,695 B2 | 9/2006 | Witt et al. |
| 7,128,720 B2 | 10/2006 | Podany |
| 7,135,030 B2 | 11/2006 | Schwemberger et al. |
| 7,163,548 B2 | 1/2007 | Stulen et al. |
| 7,179,254 B2 | 2/2007 | Pendekanti et al. |
| 7,179,271 B2 | 2/2007 | Friedman et al. |
| 7,207,997 B2 | 4/2007 | Shipp et al. |
| 7,217,128 B2 | 5/2007 | Atkin et al. |
| 7,217,893 B1 | 5/2007 | Huang et al. |
| 7,230,199 B2 | 6/2007 | Chou et al. |
| 7,244,262 B2 | 7/2007 | Wiener et al. |
| 7,269,873 B2 | 9/2007 | Brewer et al. |
| 7,273,483 B2 | 9/2007 | Wiener et al. |
| 7,300,446 B2 | 11/2007 | Beaupre |
| 7,335,997 B2 | 2/2008 | Wiener |
| 7,337,010 B2 | 2/2008 | Howard et al. |
| 7,977,587 B2 | 7/2011 | Rajagopal et al. |
| 8,435,258 B2 | 5/2013 | Young et al. |
| 8,672,959 B2 | 3/2014 | Witt et al. |
| 2001/0048855 A1 | 12/2001 | Lin |
| 2002/0002379 A1 | 1/2002 | Bishop |
| 2002/0077645 A1 | 6/2002 | Wiener et al. |
| 2002/0091339 A1 | 7/2002 | Horzewski et al. |
| 2002/0143344 A1* | 10/2002 | Taylor .................. A61B 17/66 606/105 |
| 2003/0144680 A1 | 7/2003 | Kellogg et al. |
| 2003/0149424 A1 | 8/2003 | Barlev et al. |
| 2003/0199794 A1 | 10/2003 | Sakurai et al. |
| 2003/0212363 A1 | 11/2003 | Shipp |
| 2004/0097972 A1 | 5/2004 | Shipp et al. |
| 2004/0116952 A1 | 6/2004 | Sakurai et al. |
| 2004/0256487 A1 | 12/2004 | Collins et al. |
| 2005/0091770 A1 | 5/2005 | Mourad et al. |
| 2005/0107658 A1 | 5/2005 | Brockway |
| 2005/0113815 A1 | 5/2005 | Ritchie et al. |
| 2005/0119677 A1 | 6/2005 | Shipp |
| 2005/0149063 A1 | 7/2005 | Young et al. |
| 2005/0203329 A1 | 9/2005 | Muto et al. |
| 2005/0234338 A1 | 10/2005 | Masuda |
| 2005/0234484 A1 | 10/2005 | Houser et al. |
| 2006/0058825 A1 | 3/2006 | Ogura et al. |
| 2006/0079878 A1 | 4/2006 | Houser |
| 2006/0079879 A1 | 4/2006 | Faller et al. |
| 2006/0087286 A1 | 4/2006 | Phillips et al. |
| 2006/0129168 A1 | 6/2006 | Shipp |
| 2006/0178579 A1 | 8/2006 | Haynes |
| 2006/0178667 A1 | 8/2006 | Sartor et al. |
| 2006/0194567 A1 | 8/2006 | Kelly et al. |

(56) References Cited

U.S. PATENT DOCUMENTS

| | | |
|---|---|---|
| 2006/0206100 A1 | 9/2006 | Eskridge et al. |
| 2006/0217729 A1 | 9/2006 | Eskridge et al. |
| 2007/0011836 A1 | 1/2007 | Brewer et al. |
| 2007/0149881 A1 | 6/2007 | Rabin |
| 2007/0166663 A1 | 7/2007 | Telles et al. |
| 2007/0175960 A1 | 8/2007 | Shelton et al. |
| 2007/0227866 A1 | 10/2007 | Dimig |
| 2007/0239028 A1 | 10/2007 | Houser et al. |
| 2007/0239101 A1 | 10/2007 | Kellogg |
| 2007/0282333 A1 | 12/2007 | Fortson et al. |
| 2008/0033248 A1 | 2/2008 | Akagi |
| 2008/0051693 A1 | 2/2008 | Babaev |
| 2008/0245841 A1 | 10/2008 | Smith et al. |
| 2009/0138006 A1 | 5/2009 | Bales et al. |
| 2009/0143797 A1 | 6/2009 | Smith et al. |
| 2009/0143805 A1 | 6/2009 | Palmer et al. |
| 2009/0223033 A1 | 9/2009 | Houser |
| 2010/0004669 A1 | 1/2010 | Smith et al. |
| 2010/0090420 A1 | 4/2010 | Nickels, Jr. et al. |
| 2012/0078278 A1 | 3/2012 | Bales, Jr. et al. |
| 2013/0060140 A1 | 3/2013 | Sinelnikov |
| 2013/0338691 A1 | 12/2013 | Young et al. |
| 2014/0107684 A1 | 4/2014 | Craig |
| 2015/0148830 A1 | 5/2015 | Stulen et al. |
| 2015/0245850 A1 | 9/2015 | Hibner et al. |
| 2018/0014845 A1* | 1/2018 | Dannaher ...... A61B 17/320068 |
| 2018/0014846 A1* | 1/2018 | Rhee ............. A61B 17/320092 |
| 2018/0055529 A1* | 3/2018 | Messerly ................. A61N 7/02 |
| 2019/0134429 A1* | 5/2019 | Canney .................... A61N 7/02 |

FOREIGN PATENT DOCUMENTS

| | | |
|---|---|---|
| EP | 1594209 A1 | 11/2005 |
| EP | 1707131 A1 | 10/2006 |
| EP | 2200145 A1 | 6/2010 |
| EP | 2510891 A1 | 10/2012 |
| JP | 2000506430 A | 5/2000 |
| JP | 2001112768 A | 4/2001 |
| JP | 2001514541 A | 9/2001 |
| JP | 2002518067 A | 6/2002 |
| JP | 2003502102 A | 1/2003 |
| JP | 2003285008 A | 10/2003 |
| JP | 2004129871 A | 4/2004 |
| JP | 2005278932 A | 10/2005 |
| JP | 2005296411 A | 10/2005 |
| JP | 2009538710 A | 11/2009 |
| WO | 2006087885 A1 | 8/2006 |
| WO | 2006119376 A2 | 11/2006 |
| WO | 2007047380 A2 | 4/2007 |
| WO | 2007080723 A1 | 7/2007 |

* cited by examiner

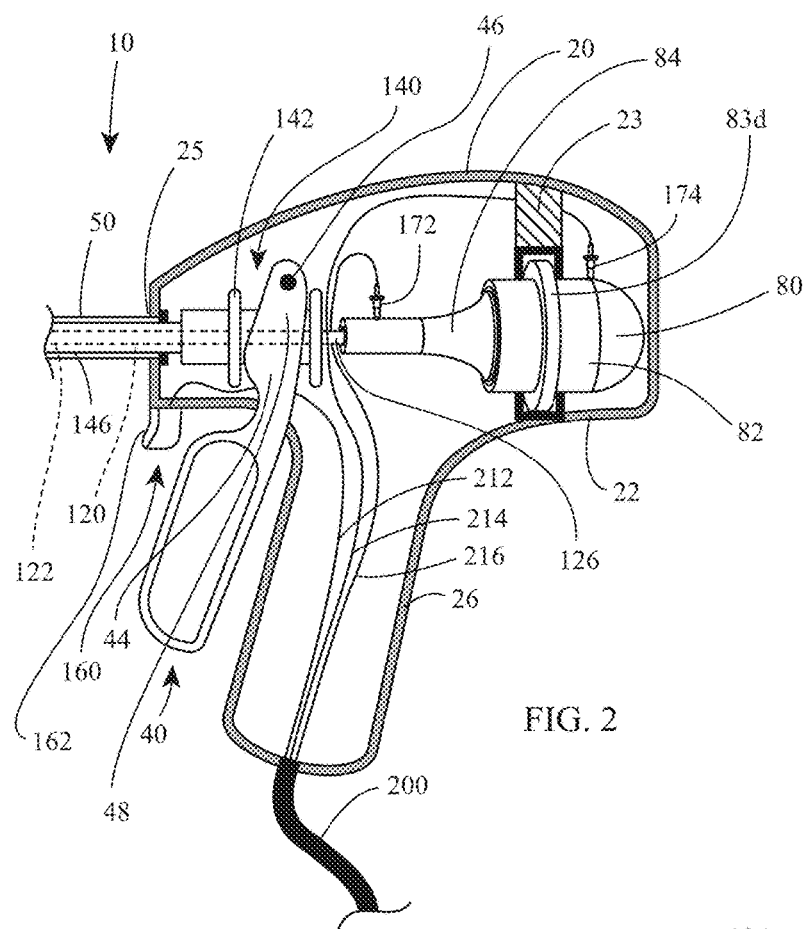
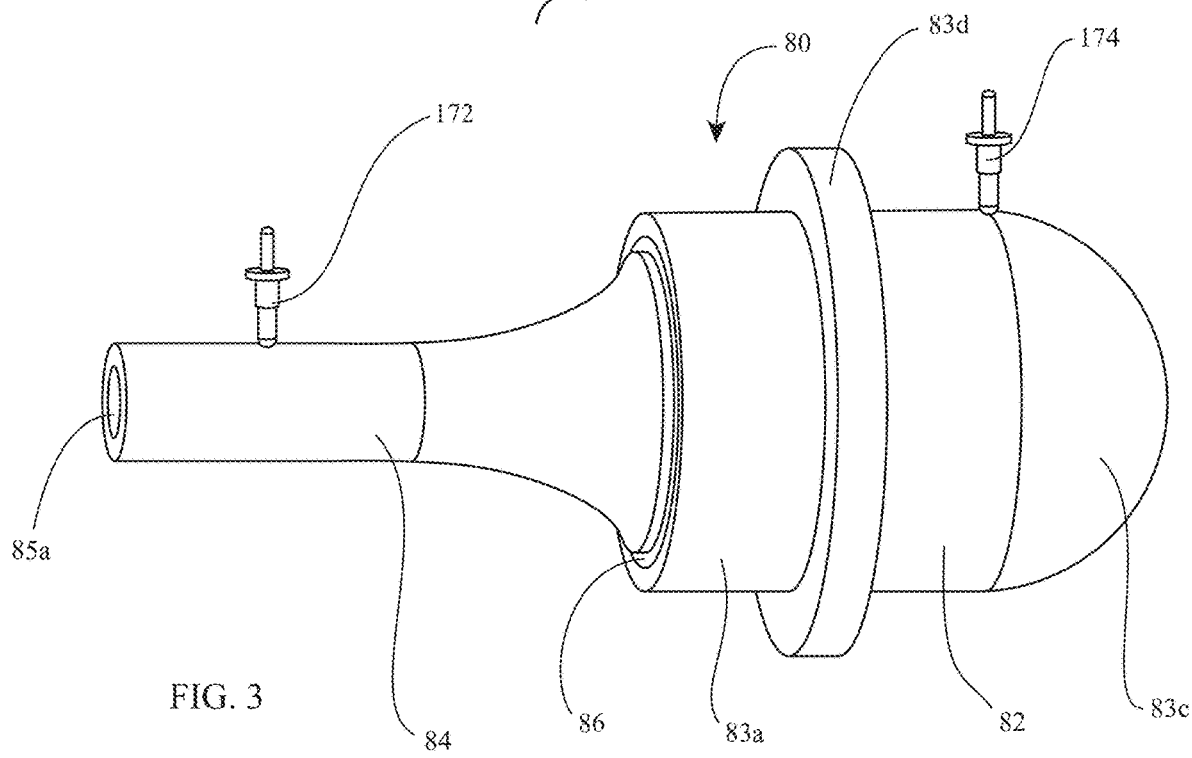
FIG. 2
FIG. 3

ULTRASONIC TRANSDUCERS AND ULTRASONIC SURGICAL INSTRUMENTS INCLUDING THE SAME

CROSS-REFERENCE TO RELATED APPLICATIONS

This application is a continuation-in-part of U.S. patent application Ser. No. 15/882,375, filed on Jan. 29, 2018, the entire contents of which is hereby incorporated herein by reference.

BACKGROUND

Technical Field

The present disclosure relates to ultrasonic surgical instruments and, more specifically, to ultrasonic transducers and ultrasonic surgical instruments including the same.

Background of Related Art

Ultrasonic surgical instruments utilize ultrasonic energy, i.e., ultrasonic vibrations, to treat tissue. More specifically, ultrasonic surgical instruments utilize mechanical vibration energy transmitted at ultrasonic frequencies to coagulate, cauterize, fuse, seal, cut, desiccate, and/or fulgurate tissue to effect hemostasis.

Ultrasonic surgical instruments typically employ a transducer coupled to a handle of the ultrasonic surgical instrument and configured to produce ultrasonic energy for transmission along a waveguide to an end effector of the ultrasonic surgical instrument that is designed to treat tissue with the ultrasonic energy. The transducer may be driven by an ultrasonic generator that is on-board, e.g., on or within the handle of the ultrasonic surgical instrument, or remotely disposed, e.g., as a set-top box connected to the ultrasonic surgical instrument via a surgical cable. The end effector of the ultrasonic surgical instrument may include a blade that receives the ultrasonic energy from the waveguide for application to tissue and a jaw member configured to clamp tissue between the blade and the jaw member to facilitate treatment thereof.

SUMMARY

As used herein, the term "distal" refers to the portion that is being described which is further from a user, while the term "proximal" refers to the portion that is being described which is closer to a user. Further, to the extent consistent any or all of the aspects detailed herein may be used in conjunction with any or all of the other aspects detailed herein.

In accordance with aspects of the present disclosure, an ultrasonic transducer for an ultrasonic surgical instrument is provided including a proximal casing defining a hollow interior, a piezoelectric rod array including a plurality of piezoelectric rods radially spaced-apart from one another, arranged in a longitudinally-oriented direction, and disposed within the hollow interior, and a distal horn including a distal connector configured to engage a waveguide. The distal horn is configured to engage the proximal casing to enclose the piezoelectric rod array within the hollow interior.

In an aspect of the present disclosure, the ultrasonic transducer further includes a seal disposed between the proximal casing and the distal horn and configured to engage the proximal casing and the distal horn with one another.

In another aspect of the present disclosure, the seal is configured to sealingly engage the proximal casing and the distal horn with one another such that the hollow interior is sealed closed.

In still another aspect of the present disclosure, the proximal casing and the distal horn are at least partially formed of an electrically-conductive material and the seal is at least partially formed from an insulative material to electrically isolate the proximal casing and the distal horn from one another. In such aspects, one of the proximal casing or the distal horn may be configured to communicate electrical energy at a first potential to the piezoelectric rod array and the other of the proximal casing or the distal horn may be configured to communicate electrical energy at a second potential to the piezoelectric rod array to energize the piezoelectric rod array.

In yet another aspect of the present disclosure, the piezoelectric rod array defines a radially-symmetric configuration relative to a longitudinal axis defined through the ultrasonic transducer.

In still yet another aspect of the present disclosure, the plurality of piezoelectric rods is maintained in compression between a proximal surface of the proximal casing and a distal surface of the distal horn.

In another aspect of the present disclosure, a distance between a center of mass of the piezoelectric rod array and the distal connector of the distal horn is one-quarter of a wavelength. Alternatively, a distance between a center of mass of the piezoelectric rod array and the distal connector of the distal horn may be another multiple of one-quarter of a wavelength.

In yet another aspect of the present disclosure, an internal cartridge is disposed within the hollow interior and configured to retain the plurality of piezoelectric rods therein.

An ultrasonic surgical instrument provided in accordance with aspects of the present disclosure includes a housing, a waveguide extending distally from the housing, an ultrasonic blade disposed at a distal end of the waveguide, and an ultrasonic transducer supported by the housing and coupled to the waveguide such that ultrasonic energy produced by the ultrasonic transducer is transmitted along the waveguide to the ultrasonic blade for treating tissue therewith. The ultrasonic transducer includes a proximal casing defining a hollow interior, a piezoelectric rod array including a plurality of piezoelectric rods radially spaced-apart from one another and arranged in a longitudinally-oriented direction in the hollow interior, and a distal horn configured to engage the proximal casing to enclose the piezoelectric rod array within the hollow interior.

In an aspect of the present disclosure, the ultrasonic transducer further includes a seal disposed between the proximal casing and the distal horn and configured to engage the proximal casing and the distal horn with one another.

In another aspect of the present disclosure, the seal is configured to sealingly engage the proximal casing and the distal horn with one another such that the hollow interior is sealed closed.

In still another aspect of the present disclosure, the proximal casing and the distal horn are at least partially formed of an electrically-conductive material and the seal is at least partially formed from an insulative material to electrically isolate the proximal casing and the distal horn from one another. In such aspects, first and second contacts may be disposed within the housing in electrical contact with the distal horn and the proximal casing, respectively, and configured to communicate electrical energy at first and second potentials to the piezoelectric rod array via the distal horn and the proximal casing, respectively, to energize the piezoelectric rod array.

In yet another aspect of the present disclosure, the ultrasonic transducer is rotatable relative to the housing and the first and second contacts and the first and second contacts maintain electrical contact with the distal horn and the proximal casing, respectively, regardless of a rotational orientation of the ultrasonic transducer relative thereto.

In still another aspect of the present disclosure, the proximal casing includes an annular flange extending radially outwardly therefrom. In such aspects, the housing includes a support configured to receive the annular flange to rotatably support the ultrasonic transducer at least partially within the housing.

In another aspect of the present disclosure, the distal horn includes a distal connector configured to engage the waveguide and a distance between a center of mass of the piezoelectric rod array and the distal connector is one-quarter of a wavelength.

In another aspect of the present disclosure, the ultrasonic surgical instrument further includes a clamp arm movable relative to the ultrasonic blade from an open position to a clamping position for clamping tissue therebetween.

In still another aspect of the present disclosure, the ultrasonic surgical instrument further includes a movable handle associated with the housing and operably coupled to the clamp arm such that actuation of the movable handle moves the clamp arm from the open position to the clamping position.

Also provided in accordance with aspects of the present disclosure is an ultrasonic transducer for an ultrasonic surgical instrument including a proximal hub, a piezoelectric rod array including a plurality of piezoelectric rods spaced-apart from one another and disposed in parallel and longitudinally-extending orientation relative to one another, and a distal horn including a distal connector configured to engage a waveguide. The proximal hub and the distal horn are configured to engage one another to retain the piezoelectric rod array therebetween under compression.

The proximal hub and the distal horn may be configured to directly or indirectly engage one another to retain the piezoelectric rod array therebetween.

In aspects of the present disclosure, a bolt is engaged between the proximal hub and the piezoelectric rod array to indirectly engaging the proximal hub and the distal horn with one another to retain the piezoelectric rod array therebetween. In such aspects, the bolt may be disposed in parallel orientation relative to the plurality of piezoelectric rods with the plurality of piezoelectric rods radially-symmetrically disposed about the bolt.

In aspects of the present disclosure, the proximal hub and the distal horn cooperate to define an enclosure enclosing the piezoelectric rod array therein.

In aspects of the present disclosure, the distal horn is configured to communicate electrical energy at a first potential to the piezoelectric rod array. The proximal hub may be configured to communicate electrical energy at a second, different potential to the piezoelectric rod array or an electrode disposed between the proximal hub and the piezoelectric rod array may be configured to communicate electrical energy at the second, different potential to the piezoelectric rod array.

In aspects of the present disclosure, an internal cartridge is disposed between the proximal hub and the distal horn and configured to retain the plurality of piezoelectric rods therein.

In aspects of the present disclosure, an ultrasonic surgical instrument includes the above-detailed ultrasonic transducer. The ultrasonic surgical instrument includes a housing, a waveguide extending distally from the housing, and an ultrasonic blade disposed at a distal end of the waveguide with the ultrasonic transducer supported by the housing and coupled to the waveguide such that ultrasonic energy produced by the ultrasonic transducer is transmitted along the waveguide to the ultrasonic blade for treating tissue therewith. The ultrasonic surgical instrument, in aspects, may further include a clamp arm movable relative to the ultrasonic blade from an open position to a clamping position for clamping tissue therebetween. Additionally, the ultrasonic surgical instrument may include a movable handle associated with the housing and operably coupled to the clamp arm such that actuation of the movable handle moves the clamp arm from the open position to the clamping position.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements and:

FIG. 2 is a side view of a proximal portion of the ultrasonic surgical instrument of FIG. 1 with components removed and wherein a portion of the housing of the ultrasonic surgical instrument is removed to illustrate the internal components therein including a ultrasonic transducer in accordance with the present disclosure;

FIG. 3 is a side, perspective view of the ultrasonic transducer of FIG. 2 including electrical contacts coupled thereto;

DETAILED DESCRIPTION

The present disclosure provides an ultrasonic transducer and ultrasonic surgical instrument including the same, although it is understood that the ultrasonic transducer of the present disclosure is equally applicable for use with other suitable surgical instruments.

Figure 1:
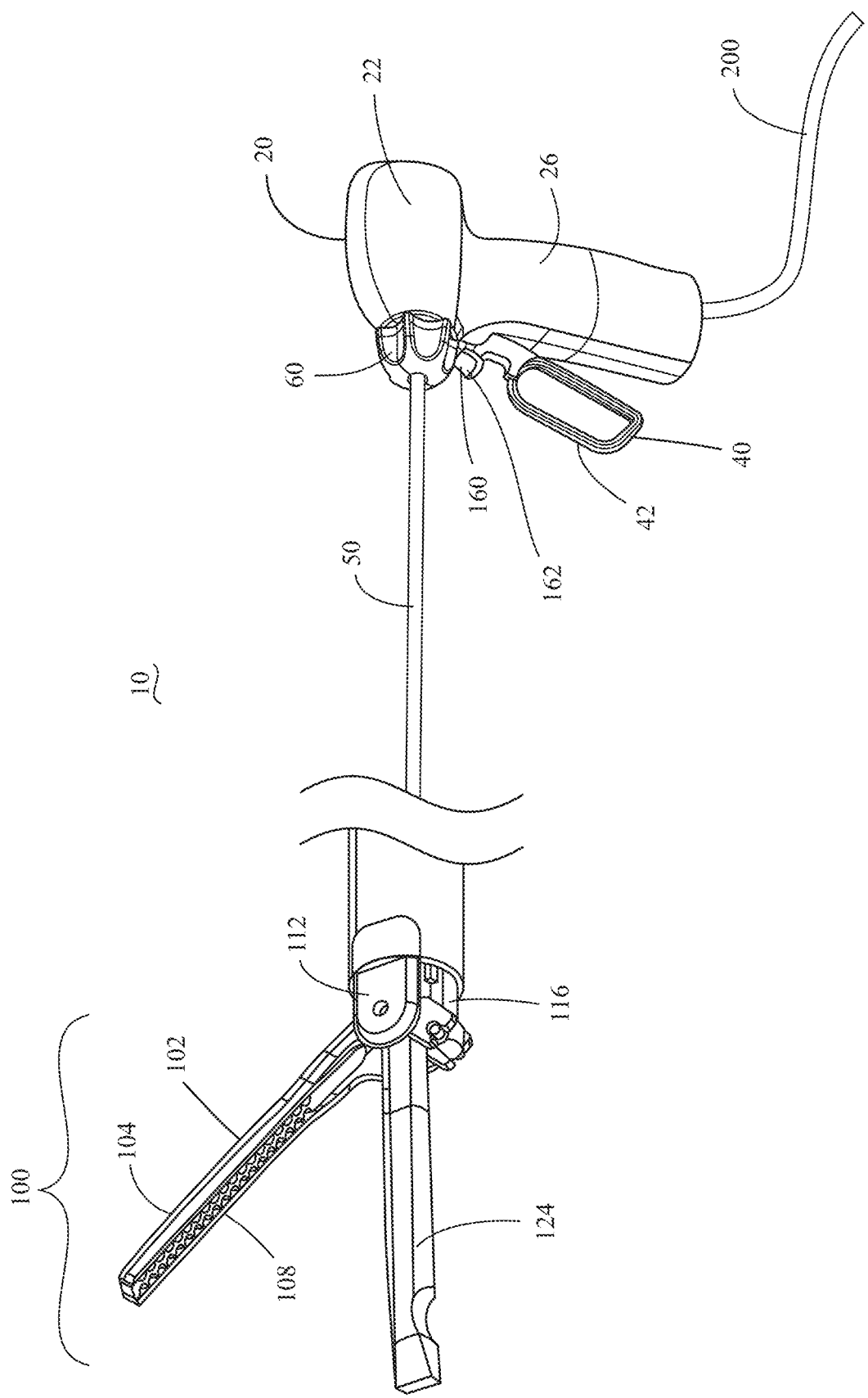
FIG. 1 is a perspective view of an ultrasonic surgical instrument provided in accordance with the present disclosure, wherein the distal end thereof is enlarged to better illustrate the components and features thereof.
Figure 4:
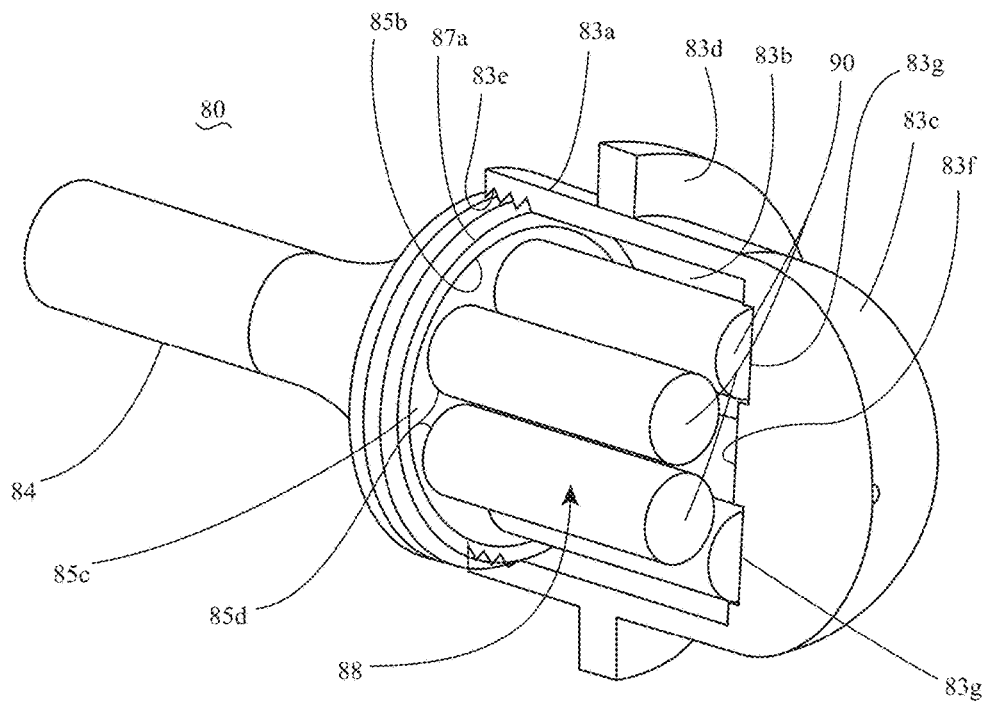
FIG. 4 is a rear, perspective view of the ultrasonic transducer of FIG. 2 with a portion removed to illustrate the internal components of the ultrasonic transducer.
Figure 5:
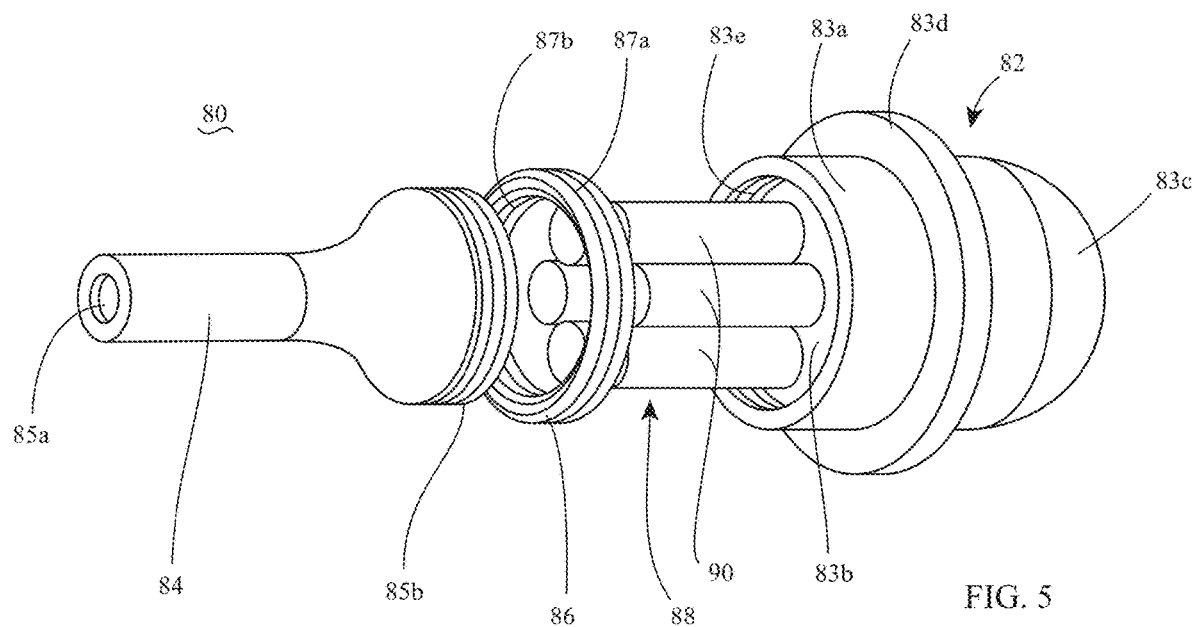
FIG. 5 is an exploded, side, perspective view of the ultrasonic transducer of FIG. 2.

Referring to FIGS. 1 and 2, an ultrasonic surgical instrument configured for use in accordance with the aspects and features of the present disclosure is shown generally identified by reference numeral 10. Ultrasonic surgical instrument 10 includes a housing 20, a movable handle 40 operably coupled to housing 20, a shaft 50 extending distally from housing 20, a rotation knob 60 supported on housing 20 and configured for rotating shaft 50 relative to housing 20, and an ultrasonic transducer 80 (FIG. 2) in accordance with the present disclosure supported within housing 20. Ultrasonic surgical instrument 10 further includes an end effector assembly 100 disposed at a distal end of shaft 50, a waveguide 120 (FIG. 2) extending through housing 20 and shaft 50 and operably coupling ultrasonic transducer 80 to end effector assembly 100, a drive assembly 140 (FIG. 2) operably coupled between movable handle 40 and end effector assembly 100, and an activation assembly 160 operably coupled to housing 20 for selectively supplying energy to ultrasonic transducer 80 to drive ultrasonic transducer 80. Ultrasonic surgical instrument 10 additionally includes a cable 200 configured to connect to a generator (not shown) or other power source for driving ultrasonic transducer 80.

Housing 20 defines a longitudinally-extending barrel portion 22 and a fixed handle portion 26 extending downwardly from barrel portion 22 in generally perpendicular orientation relative thereto. Barrel portion 22 of housing 20 defines a support 23 configured to rotatably support ultrasonic transducer 80 at least partially within housing 20. In embodiments, ultrasonic transducer 80 is removable from housing 20. ultrasonic transducer 80 is described in detail below. Barrel portion 22 further defines a distal opening 25 through which shaft 50, the drive sleeve 146 of drive assembly 140, and waveguide 120 extend in substantially coaxial arrangement. Fixed handle portion 26 of housing 20 is positioned adjacent movable handle 40 to enable a user to grasp fixed handle portion 26 of housing 20 and manipulate movable handle 40 with a single hand.

Movable handle 40 includes a grasping portion 42 configured to facilitate grasping and manipulation by a user. Movable handle 40 further includes a flange portion 44 extending into barrel portion 22 of housing 20. Flange portion 44 is pivotably coupled to housing 20 via a pivot pin 46 and defines a bifurcated configuration including first and second spaced-apart flange arms 48 (only one flange arm 48 is illustrated in FIG. 2 as it obscures the other flange arm 48) operably couple to mandrel 142 of drive assembly 140 such that pivoting of movable handle 40 relative to housing 20 about pivot pin 46 from a spaced-apart position towards an approximated position translates drive sleeve 146 of drive assembly 140 relative to end effector assembly 100 to pivot clamp arm 102 of end effector assembly 100 relative to blade 124 of end effector assembly 100 between an open position and a clamping position for clamping tissue therebetween.

With continued reference to FIGS. 1 and 2, shaft 50 is rotatably supported by housing 20 and extends distally through distal opening 25 of barrel portion 22 of housing 20. Shaft 50 includes end effector assembly 100 disposed at a distal end thereof. Shaft 50 is disposed about drive sleeve 146 of drive assembly 140, although it is also contemplated that this configuration be reversed, e.g., wherein drive sleeve 146 is disposed about shaft 50. Shaft 50 is longitudinally fixed relative to housing 20 but is rotatable relative thereto in response to rotation of rotation knob 60 relative to housing 20 via coupling therebetween. Rotation knob 60 is also coupled to drive sleeve 146 and waveguide 120 such that rotation of rotation knob 60 likewise rotates drive assembly 140, waveguide 120, and ultrasonic transducer 80 relative to housing 20 in response to rotation of rotation knob 60 relative to housing 20.

End effector assembly 100 includes clamp arm 102, blade 124 of waveguide 120, a pair of clevis members 112 (only one clevis member 112 is illustrated in FIG. 1 with the other being obstructed), and a drive link 116. Clamp arm 102 includes a frame 104 and a tissue pad 108 engaged with frame 104. Frame 104 of clamp arm 102 is pivotably coupled to a distal end portion of shaft 50 by way of clevis members 112. Drive link 116 is coupled between frame 104 of clamp arm 102 and a distal end portion of drive sleeve 146 (FIG. 2) such that translation of drive sleeve 146 translates drive link 116 to thereby pivot clamp arm 102 between the open and clamping positions.

Waveguide 120 defines a body 122, a blade 124 extending from the distal end of body 122, and a proximal connector 126 extending from the proximal end of body 122. Blade 124 extends distally from drive sleeve 146 of drive assembly 140 and shaft 50 and, as noted above, forms part of end effector assembly 100 in that blade 124 is positioned to oppose clamp arm 102 such that pivoting of clamp arm 102 from the open position to the clamping position enables clamping of tissue between clamp arm 102 and blade 124. Blade 124 may define a linear configuration as shown, or may define a curved configuration. Proximal connector 126 of waveguide 120 is configured to enable engagement of waveguide 120 with ultrasonic transducer assembly 80, e.g., via a threaded engagement, such that mechanical motion produced by ultrasonic transducer assembly 80 is capable of being transmitted along waveguide 120 to blade 124 for treating tissue clamped between blade 124 and clamp arm 102 or positioned adjacent blade 124.

Drive assembly 140 includes mandrel 142 operably disposed about drive sleeve 146. Mandrel 142 is configured to receive flange portion 44 of movable handle 40 such that pivoting of movable handle 40 imparts longitudinal motion to mandrel 142. Longitudinal motion of mandrel 142, in turn, translates drive sleeve 146 to pivot clamp arm 102 between the open and clamping positions. Mandrel 142 may be fixedly coupled to drive sleeve 146 or may be coupled thereto via a force-limiting connection (not shown) to limit a clamping force applied to tissue disposed between clamp arm 102 and blade 124.

Activation assembly 160 includes an activation button 162 extending from housing 20 to enable manual manipulation by a user. In some embodiments, activation button 162 is configured as a two-mode button wherein actuation of button 162 to a first actuated position supplies energy to ultrasonic transducer 80 corresponding to a "LOW" power mode, and wherein actuation of button 162 to a second actuated position supplies energy to ultrasonic transducer 80 corresponding to a "HIGH" power mode.

Wires 212, 214, 216 extending through cable 200 are configured to electrically couple the generator (not shown) with activation button 162 and first and second contacts 172, 174 for driving ultrasonic transducer 80 upon activation of activation button 162, e.g., in either the "LOW" power mode or the "HIGH" power mode. First and second contacts 172, 174 are fixed within housing 20 and configured such that first and second contacts 172, 174 remain electrically coupled to ultrasonic transducer 80 regardless of the rotational orientation of ultrasonic transducer 80 relative to housing 20.

Figure 6:
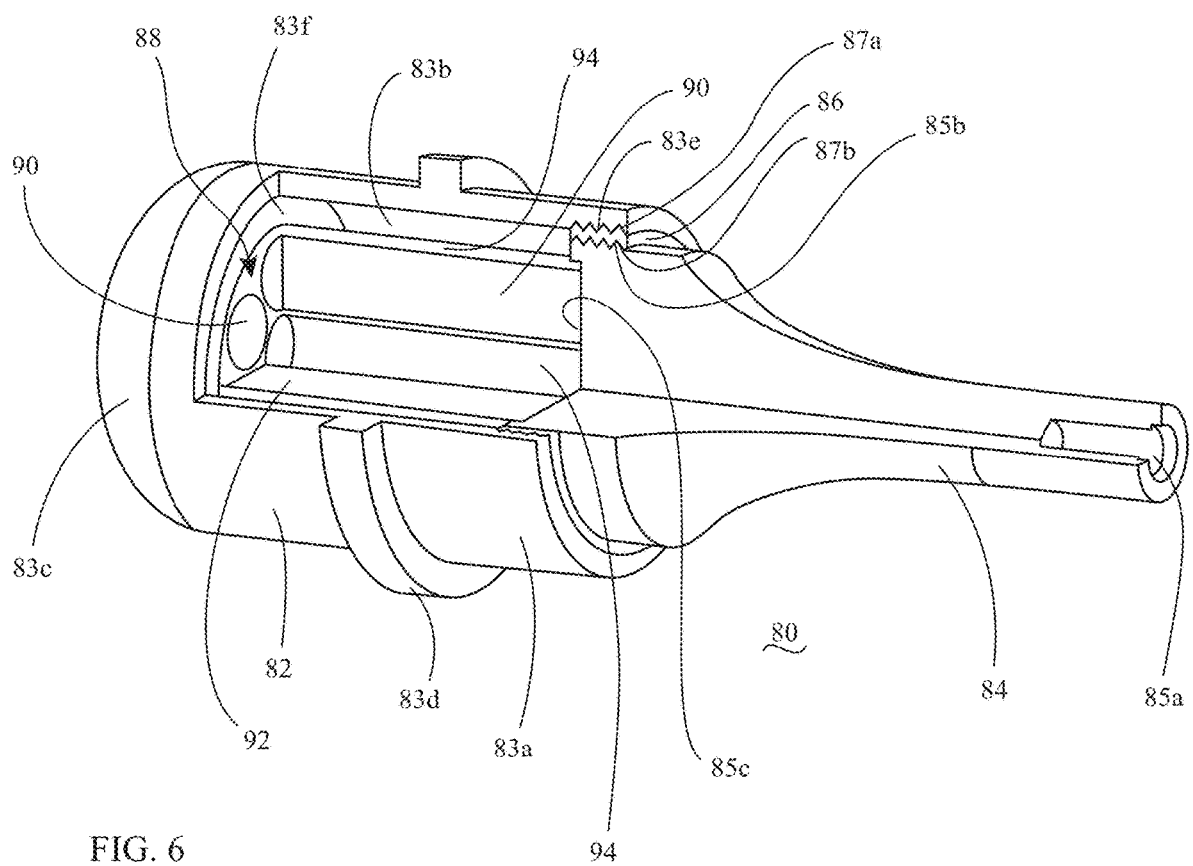
FIG. 6 is a perspective, partial cross-sectional view of the ultrasonic transducer of FIG. 2 including an interior cartridge retaining the piezoelectric rods therein.

Turning now to FIGS. 3-6, ultrasonic transducer 80 is detailed. Ultrasonic transducer 80 includes a proximal hub (in the form of a proximal casing 82), a distal horn 84, an isolating seal 86, a piezoelectric rod array 88 including a plurality of piezoelectric rods 90, and, in embodiments, an internal cartridge 92 (FIG. 6).

Proximal casing 82 of ultrasonic transducer 80 includes a tubular body 83a defining a hollow interior 83b, a solid semi-spherical proximal cap 83c closing the proximal end of tubular body 83a, and an annular flange 83d disposed about and extending radially outwardly from an exterior surface of tubular body 83a. Proximal casing 82 is formed from an electrically-conductive material and may be monolithically formed as a single piece of material, or otherwise formed such that proximal cap 83a is sealed to the proximal end of tubular body 83a. Annular flange 83d enables rotatable mounting of ultrasonic transducer 80 within housing 20 via support 23 of housing 20 (see FIG. 2). Tubular body 83a defines a generally smooth surface in the vicinity of second contact 174 of ultrasonic surgical instrument 10 such that electrical communication is maintained between tubular body 83a and second contact 174 regardless of the rotational orientation of ultrasonic transducer 80 relative to second contact 1740 (see FIG. 2). Threading 83e is formed on the interior annular surface of tubular body 83a towards the distal end of tubular body 83a, the purpose of which is detailed below. In embodiments, an internal, distally-facing surface 83f of proximal cap 83a defines a plurality of cylindrical-shaped indentations 83g, each configured to support a proximal end of one of the piezoelectric rods 90 therein in complementary-fit engagement therewith. In other embodiments, indentations 83g are not provided and surface 83f defines a planar configuration. In either configuration, the proximal ends of piezoelectric rods 90 are electrically coupled with second contact 174 via the electrically-conductive proximal casing 82.

Distal horn 84 of ultrasonic transducer 80 is formed from an electrically-conductive material and may be monolithically formed as a single piece of solid material, or may otherwise be formed and/or configured. Distal horn 84 tapers in a proximal-to-distal direction and defines a distal connector 85a configured to receive proximal connector 126 of waveguide 120 (FIG. 2) therein, e.g., via male-female threaded connection, to operably couple distal horn 84 and, thus, ultrasonic transducer 80, with waveguide 120 (FIG. 2). Distal horn 84 further includes threading 85b formed on the exterior annular surface thereof towards the proximal end thereof, the purpose of which is detailed below. Distal horn 84 also defines a generally smooth surface in the vicinity of first contact 172 of ultrasonic surgical instrument 10 such that electrical communication is maintained between distal horn 84 and first contact 172 regardless of the rotational orientation of ultrasonic transducer 80 relative to first contact 172 (see FIG. 2).

Distal horn 84 additionally defines a proximally-facing surface 85c. Proximally-facing surface 85c may define a plurality of cylindrical-shaped indentations 85d, each configured to support a distal end of one of the piezoelectric rods 90 therein in complementary-fit engagement therewith. In other embodiments, indentations 85d are not provided and surface 85c defines a planar configuration. In either configuration, the distal ends of piezoelectric rods 90 are electrically coupled with first contact 172 via the electrically-conductive distal horn 84.

Isolating seal 86 is formed from an electrically-insulative material and defines a ring-shaped configuration having external threading 87a defined on an outer annular surface thereof and internal threading 87b defined on an inner annular surface thereof. External threading 87a is configured to engage threading 83e of proximal casing 82 and internal threading 87b is configured to engage threading 85b of distal horn 84 to thereby sealingly engage proximal casing 82 and distal horn 84 with one another, thereby sealing off hollow interior 83b of proximal casing 82 while maintaining proximal casing 82 and distal horn 84 electrically isolated from one another.

Continuing with reference to FIGS. 3-6, piezoelectric rod array 88, as noted above, includes a plurality of piezoelectric rods 90. Piezoelectric rods 90 are arranged in a longitudinally-oriented direction, substantially parallel (within manufacturing and material tolerances) to a longitudinal axis of ultrasonic transducer 80, and may be arranged in a radially-symmetric or other suitable pattern. Although six (6) piezoelectric rods 90 (in FIGS. 4 and 5, wherein there is no central rod) or seven (7) piezoelectric rods 90 (in FIG. 6, wherein a central rod is provided) are shown, greater or fewer piezoelectric rods 90 are also contemplated. Piezoelectric rods 90 are configured for positioning within the sealed hollow interior 83b of proximal casing 82 with the proximal ends thereof in contact with (and thus electrically communication with) surface 83f of proximal casing 82 and the distal ends thereof in contact with (and thus electrically communication with) surface 85c of distal horn 84 such that piezoelectric rods 90 are under compression.

In embodiments, receipt of the proximal and distal ends of piezoelectric rods 90 within indentations 83g, 85d, respectively, serves to maintain piezoelectric rods 90 in position. Alternatively or additionally, as illustrated in FIG. 6, internal cartridge 92 defining a plurality of rod-receiving receptacles 94 may be disposed within hollow interior 83b of proximal casing 82 to maintain piezoelectric rods 90 in position.

As a result of the above-detailed configuration, ultrasonic transducer 80 may define a length wherein a distance between the center of mass of piezoelectric rod array 88 and distal connector 85a of distal horn 84 is one-quarter ($\frac{1}{4}$) of a wavelength. Ultrasonic transducer 80 may alternatively define a greater such length in one-quarter ($\frac{1}{4}$) wavelength intervals. The above-detailed configuration also seals ultrasonic transducer 80 to enable ultrasonic transducer 80 to be autoclaved, cleaned, and/or otherwise sterilized for repeated use.

In use, upon activation, one of the contacts, e.g., first contact 172, serves as the ground (neutral) electrode and the other contact, e.g., second contact 174, serves as the alternating charged (+/−) electrode to energize piezoelectric rods 90, thereby producing ultrasonic energy, e.g., mechanical vibration motion, that is transmitted from piezoelectric rods 90 through distal horn 84 and waveguide 120 (FIG. 2) to blade 124 (FIG. 1) for treating tissue therewith.

Figure 7A:
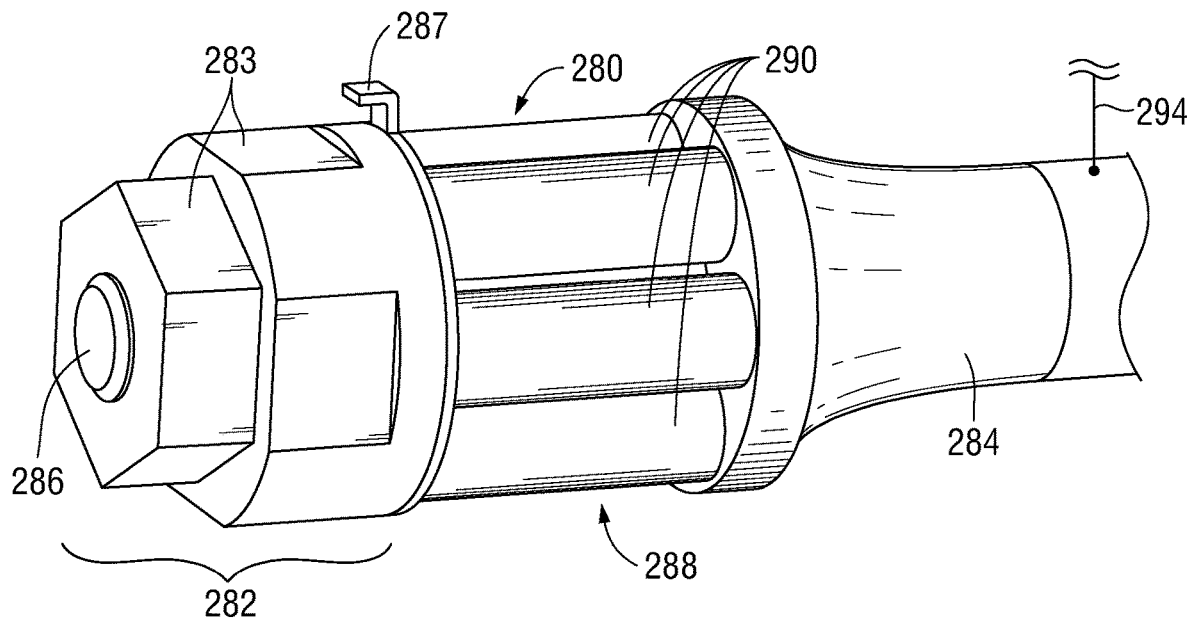
FIG. 7A is a rear, perspective view of another ultrasonic transducer provided in accordance with the present disclosure and configured for use with the ultrasonic surgical instrument of FIG. 1 or any other suitable ultrasonic surgical instrument.
Figure 7B:
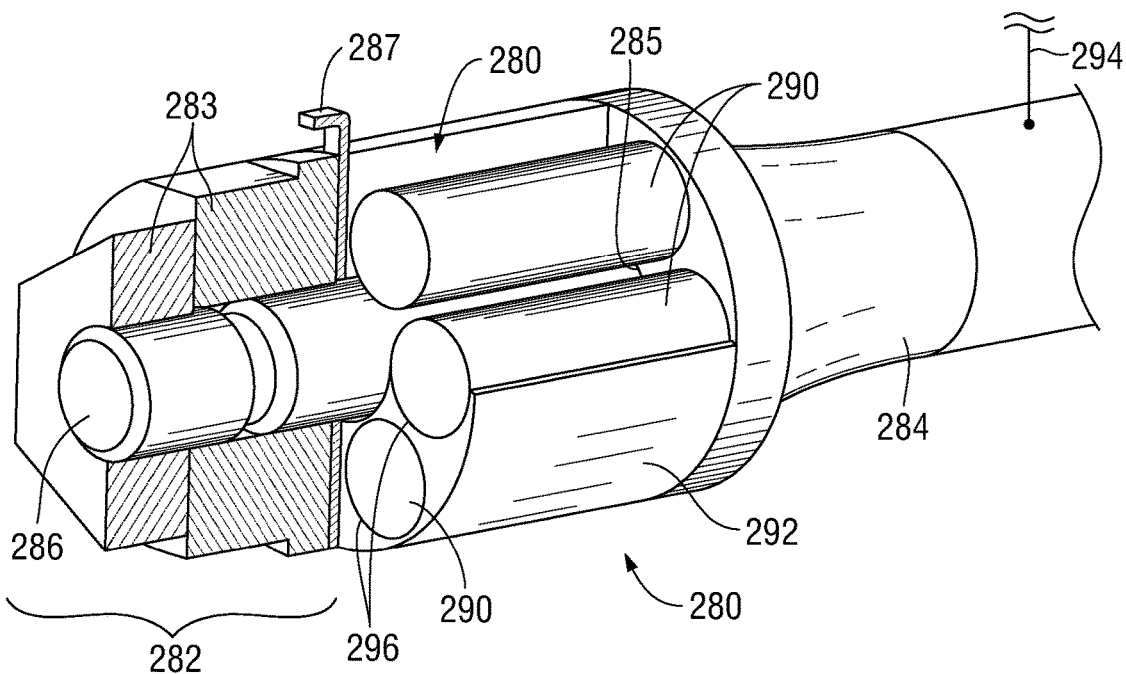
FIG. 7B is a rear, a perspective, partial cross-sectional view of the ultrasonic transducer of FIG. 7A including an interior cartridge retaining the piezoelectric rods therein.

Turning now to FIGS. 7A and 7B, another ultrasonic transducer 280 provided in accordance with the present disclosure and configured for use with ultrasonic surgical instrument 10 (FIG. 1), similarly as detailed above with respect to ultrasonic transducer 80 (FIGS. 2-6), or another suitable ultrasonic surgical instrument, is detailed. Ultrasonic transducer 280 is similar to and may include any of the features of ultrasonic transducer 80 (FIGS. 2-6), except as explicitly contradicted below. Ultrasonic transducer 280 generally includes a proximal hub 282, a distal horn 284, a bolt 286, an electrode 287, a piezoelectric rod array 288 including a plurality of piezoelectric rods 290, and, in embodiments, an internal cartridge 292 (FIG. 7B).

Proximal hub 282 of ultrasonic transducer 280 may include one or more components 283, e.g., a nut (more proximal) and a base (more disatlproximal base, each defining an aperture therethrough for receipt and retention of a proximal portion of bolt 286 such that bolt 286 is inhibited from passing completely through proximal hub 282 in a distal direction. Electrode 287 abuts the distally-facing surface of proximal hub 282. The proximal ends of piezoelectric rods 290, in turn, abut electrode 287, thus establishing electrical communication therewith.

Distal horn 284 of ultrasonic transducer 280 is formed from an electrically-conductive material and may be monolithically formed as a single piece of solid material, or may otherwise be formed and/or configured. The distal ends of piezoelectric rods 290 abut the proximally-facing surface of distal horn 284, thus establishing electrical communication therewith. Distal horn 284 defines a proximally-facing bore 285 which may include internal threading (not shown) or other suitable features to receive and secure the distal end of bolt 286 therein such that bolt 286 retains piezoelectric rods 290 between distal horn 284 and proximal hub 282 under compression (with electrode 287 disposed between piezoelectric rods 290 and proximal hub 282).

Continuing with reference to FIGS. 7A and 7B, piezoelectric rod array 288 includes a plurality of piezoelectric rods 290 arranged in a longitudinally-oriented direction, substantially parallel (within manufacturing and material tolerances) to a longitudinal axis of ultrasonic transducer 280, spaced-apart from one-another, and, in embodiments, arranged in a radially-symmetric or other suitable pattern. Although six (6) piezoelectric rods 290 are shown, greater or fewer piezoelectric rods 290 are also contemplated, as are various different cross-sectional configurations, e.g., circular, triangular, star-shaped, rectangular, etc. Piezoelectric rods 290, as noted above, are held between distal horn 284 and proximal hub 282 under compression and in electrical communication with electrode 287 and distal horn 284 at the respective proximal and distal ends thereof. As such, electrode 287 may be connected to a first potential and distal horn 284 to a second potential, e.g., via an electrical connector 294, to energize piezoelectric rods 290 to drive ultrasonic transducer 280. In embodiments, bolt 286 extends in parallel orientation relative to piezoelectric rods 290 with piezoelectric rods 290 radially-symmetrically disposed thereabout.

Internal cartridge 292, in embodiments where provided, defines a plurality of rod-receiving receptacles 296 configured to receive and maintain piezoelectric rods 290 in position.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ultrasonic transducer for an ultrasonic surgical instrument, the ultrasonic transducer comprising:
   a proximal hub including an internal cartridge, the internal cartridge defining a plurality of indentations arranged in a radial pattern;
   a piezoelectric rod array including a plurality of piezoelectric rods, an end portion of each piezoelectric rod of the plurality of piezoelectric rods configured to be inserted into one of the indentations of the plurality of indentations defined within the internal cartridge such that the plurality of piezoelectric rods are disposed about a longitudinal axis of a waveguide,
      wherein each indentation of the plurality of indentations defined within the internal cartridge extends distally from the proximal hub along an axis parallel to the longitudinal axis of the waveguide, such that each piezoelectric rod of the plurality of piezoelectric rods is oriented along an axis parallel to the longitudinal axis; and
   a distal horn including a distal connector configured to engage the waveguide, the distal horn defining a longitudinal axis aligned with the longitudinal axis of the waveguide when engaged therewith, the proximal hub and the distal horn configured to engage one another to retain the piezoelectric rod array therebetween under compression,
      wherein the internal cartridge is disposed between the proximal hub and the distal horn and configured to retain the plurality of piezoelectric rods therein.

2. The ultrasonic transducer according to claim 1, wherein the proximal hub and the distal horn are configured to directly engage one another to retain the piezoelectric rod array therebetween.

3. The ultrasonic transducer according to claim 1, wherein the proximal hub and the distal horn are configured to indirectly engage one another to retain the piezoelectric rod array therebetween.

4. The ultrasonic transducer according to claim 3, further comprising a bolt engaged between the proximal hub and the piezoelectric rod array, the bolt indirectly engaging the proximal hub and the distal horn with one another to retain the piezoelectric rod array therebetween.

5. The ultrasonic transducer according to claim 4, wherein the bolt is disposed in parallel orientation relative to the plurality of piezoelectric rods with the plurality of piezoelectric rods radially-symmetrically disposed about the bolt.

6. The ultrasonic transducer according to claim 1, wherein the proximal hub and the distal horn cooperate to define an enclosure enclosing the piezoelectric rod array therein.

7. The ultrasonic transducer according to claim 1, wherein the distal horn is configured to communicate electrical energy at a first potential to the piezoelectric rod array.

8. The ultrasonic transducer according to claim 7, wherein the proximal hub is configured to communicate electrical energy at a second, different potential to the piezoelectric rod array.

9. The ultrasonic transducer according to claim 7, further comprising an electrode disposed between the proximal hub and the piezoelectric rod array, the electrode configured to communicate electrical energy at a second, different potential to the piezoelectric rod array.

10. An ultrasonic surgical instrument, comprising:
    a housing;
    a waveguide extending distally from the housing;
    an ultrasonic blade disposed at a distal end of the waveguide; and
    an ultrasonic transducer supported by the housing and coupled to the waveguide such that ultrasonic energy produced by the ultrasonic transducer is transmitted along the waveguide to the ultrasonic blade for treating tissue therewith, the ultrasonic transducer including:
       a proximal hub including an internal cartridge, the internal cartridge defining a plurality of indentations arranged in a radial pattern;
       a piezoelectric rod array including a plurality of piezoelectric rods, an end portion of each piezoelectric rod of the plurality of piezoelectric rods configured to be inserted into one of the indentations of the plurality of indentations defined within the internal cartridge such that the plurality of piezoelectric rods are disposed about a longitudinal axis of a waveguide,
          wherein each indentation of the plurality of indentations defined within the internal cartridge extends distally from the proximal hub along an axis parallel to the longitudinal axis of the waveguide, such that each piezoelectric rod of the plurality of piezoelectric rods is oriented along an axis parallel to the longitudinal axis; and a distal horn including a distal connector configured to engage the waveguide, the distal horn defining a longitudinal axis aligned with the longitudinal axis of the waveguide when engaged therewith, the proximal hub and the distal horn configured to engage one another to retain the piezoelectric rod array therebetween under compression, wherein the internal cartridge is disposed between the proximal hub and the distal horn and configured to retain the plurality of piezoelectric rods therein.

11. The ultrasonic surgical instrument according to claim 10, wherein the proximal hub and the distal horn are configured to directly engage one another to retain the piezoelectric rod array therebetween.

12. The ultrasonic surgical instrument according to claim 10, wherein the proximal hub and the distal horn are configured to indirectly engage one another to retain the piezoelectric rod array therebetween.

13. The ultrasonic surgical instrument according to claim 12, further comprising a bolt engaged between the proximal hub and the piezoelectric rod array, the bolt indirectly engaging the proximal hub and the distal horn with one another to retain the piezoelectric rod array therebetween.

14. The ultrasonic surgical instrument according to claim 10, wherein the proximal hub and the distal horn cooperate to define an enclosure enclosing the piezoelectric rod array therein.

15. The ultrasonic surgical instrument according to claim 10, wherein the distal horn is configured to communicate electrical energy at a first potential to the piezoelectric rod array.

16. The ultrasonic surgical instrument according to claim 15, wherein the proximal hub is configured to communicate electrical energy at a second, different potential to the piezoelectric rod array.

17. The ultrasonic surgical instrument according to claim 15, further comprising an electrode disposed between the proximal hub and the piezoelectric rod array, the electrode configured to communicate electrical energy at a second, different potential to the piezoelectric rod array.

18. The ultrasonic surgical instrument according to claim 10, further comprising a clamp arm movable relative to the ultrasonic blade from an open position to a clamping position for clamping tissue therebetween.

19. The ultrasonic surgical instrument according to claim 18, further comprising a movable handle associated with the housing and operably coupled to the clamp arm such that actuation of the movable handle moves the clamp arm from the open position to the clamping position.

* * * * *